United States Patent [19]

Schlegel et al.

[11] Patent Number: 5,374,725
[45] Date of Patent: Dec. 20, 1994

[54] PROCESS FOR THE PREPARATION OF SULFONYLUREAS

[75] Inventors: Günter Schlegel, Liederbach; Hilmar Mildenberger, Kelkheim, both of Germany

[73] Assignee: Hoechst Aktiengesellschaft, Frankfurt am Main, Germany

[21] Appl. No.: 200,920

[22] Filed: Feb. 22, 1994

Related U.S. Application Data

[63] Continuation of Ser. No. 861,255, Mar. 31, 1992, abandoned.

[30] Foreign Application Priority Data

Apr. 2, 1991 [DE] Germany .................. 4110636

[51] Int. Cl.$^5$ .................. C07D 251/54; C07D 251/48; C07D 251/42; C07D 239/42
[52] U.S. Cl. .................. 544/197; 544/199; 544/213; 544/211; 544/210; 544/208; 544/206; 544/205; 544/320; 544/321; 544/323; 544/332
[58] Field of Search .................. 544/196, 197, 199, 205, 544/206, 208, 207, 210, 211, 213, 320, 323, 332, 321

[56] References Cited

U.S. PATENT DOCUMENTS

| | | | |
|---|---|---|---|
| 3,232,981 | 2/1966 | Haack et al. ............ | 260/553 |
| 3,409,644 | 11/1968 | Müller et al. . | |
| 3,931,277 | 1/1976 | Lohaus . | |
| 4,191,553 | 3/1980 | Reap ............ | 71/92 |
| 4,391,976 | 7/1983 | Böhner ............ | 544/211 |
| 4,509,972 | 4/1985 | Mengel et al. ............ | 71/92 |
| 4,534,790 | 8/1985 | Wolf ............ | 71/93 |
| 4,601,747 | 7/1986 | Willms ............ | 71/92 |
| 4,718,937 | 1/1988 | Willms ............ | 71/93 |

FOREIGN PATENT DOCUMENTS

| | | |
|---|---|---|
| 0004163 | 6/1982 | European Pat. Off. . |
| 0091593 | 3/1983 | European Pat. Off. . |
| 0232067 | 8/1987 | European Pat. Off. . |
| 0342569 | 5/1989 | European Pat. Off. . |
| 0388994 | 9/1990 | European Pat. Off. . |
| 1164398 | 3/1964 | Germany . |
| 1201337 | 9/1965 | Germany . |
| 3105453 | 10/1982 | Germany . |

OTHER PUBLICATIONS

Houben–Weyl, p. 1015, "*Methoden der Organischen Chemie*", 1983, 334–344.
Chem. Berichte (105) 2792-9 (1972) (Birkofer et al).
J. Chem. Comm, p. 527 (1968) (Thaler).

*Primary Examiner*—John M. Ford
*Attorney, Agent, or Firm*—Curtis, Morris & Safford

[57] ABSTRACT

A compound of formula I or salt thereof can be prepared in a process which comprises reacting a compound of formula II with a compound of formula III:

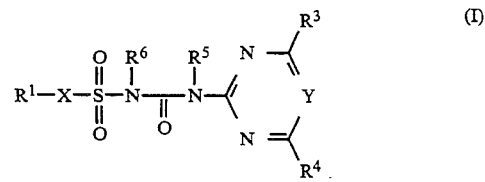

(I)

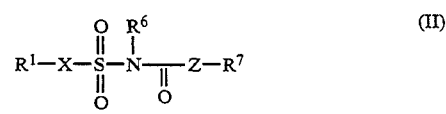

(II)

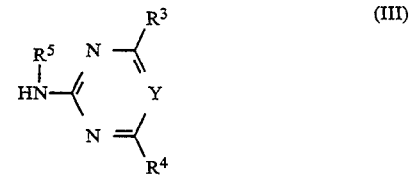

(III)

wherein the formulae I-III the radical X is O, ONR$^2$ or SO$_2$NR$^2$; Y is N or CH;
  R$^1$ is (subst.) alkyl, (subst.) alkenyl, (subst.) alkynyl, or in case X=O, also (subst.) phenyl;
  R$^2$ is H, alkyl, alkenyl, alkynyl or cycloalkyl,
  R$^3$-R$^6$ are defined in claim 1;
  Z is S or NR$^8$; R$^7$, R$^8$ are H, alkyl, (subst.) phenyl or (subst.) benzyl, or, in case Z=NR$^8$, R$^7$ and NR$^8$ are also a 5- to 7-membered heterocycle.

9 Claims, No Drawings

PROCESS FOR THE PREPARATION OF SULFONYLUREAS

This application is a continuation of application Ser. No. 07/861,255, filed Mar. 31, 1992, now abandoned.

The invention relates to processes for the preparation of herbicides from the group comprising the heterocyclically substituted sulfonylureas, specifically the compounds of the formula I

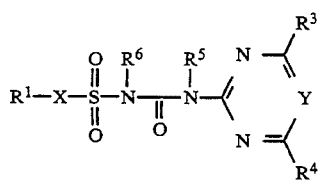

in which

X is oxygen, —O—$NR^2$— or —$SO_2$—$NR^2$—,

Y is a nitrogen atom or CH, $R^1$ is $(C_1-C_6)$-alkyl, $(C_2-C_6)$-alkenyl or $(C_2-C_6)$-alkynyl, where each of the 3 radicals is unsubstituted or mono- or polysubstituted by radicals selected from the group comprising halogen, $(C_1-C_4)$-alkoxy and $(C_1-C_4)$-alkoxycarbonyl, or, in the case where X is oxygen, also phenyl which is unsubstituted or substituted by one or more radicals selected from the group comprising halogen, nitro, $(C_1-C_4)$-alkyl, $(C_1-C_4)$-haloalkyl, $(C_1-C_4)$-alkoxy, $(C_1-C_4)$-haloalkoxy or $(C_2-C_4)$-alkoxycarbonyl, $R^2$ is hydrogen, $(C_1-C_6)$-alkyl, $(C_2-C_6)$-alkenyl, $(C_2-C_6)$-alkynyl or $(C_3-C_6)$-cycloalkyl, $R^3$ and $R^4$ independently of one another are hydrogen, $(C_1-C_4)$-alkyl or $(C_1-C_4)$-alkoxy, where each of the two last-mentioned radicals is unsubstituted or mono- or polysubstituted by radicals selected from the group comprising halogen, alkoxy and alkylthio, or are halogen, $(C_1-C_4)$-alkylthio, $(C_1-C_4)$-alkylamino or di-$[(C_1-C_4)$-alkyl]-amino and $R^5$ and $R^6$ independently of one another are hydrogen or $(C_1-C_4)$-alkyl and, if one or each of the radicals $R^5$ and $R^6$ is hydrogen, their physiologically acceptable salts with acids or bases.

Compounds of the formula I are known and are employed as crop protection agents which have a herbicidal action; see EP-A-0,131,258, EP-A-0,342,569 and EP-A-4,163. These publications also describe, or cite, a number of processes by means of which compounds of the formula I can be prepared.

The disadvantage in the known processes are the relatively poor yields of approximately 65–70% at most. This gives rise to comparatively large amounts of impurities and by-products which, when the processes are used on an industrial scale, constitute waste materials whose disposal involves complex procedures, for example incineration. The known processes are therefore unsuitable for industrial scale production, both from the ecological and the economical point of view. Moreover, such poor yields mean a considerable wastage of the starting materials employed, which reduces the efficiency of the processes.

There has now been found a novel process which allows the compounds of the formula I to be prepared in surprisingly high yield and purity and which is suitable for industrial scale production.

The present invention relates to a process for the preparation of the abovementioned compounds of the formula I or their salts, which comprises reacting compounds of the formula II

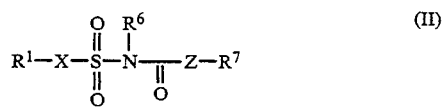

in which

Z is a sulfur atom or a group of the formula —$NR^8$— and $R^7$ and $R^8$ independently of one another are hydrogen, $(C_1-C_6)$-alkyl, phenyl or benzyl, the above-mentioned aromatic radicals being unsubstituted or substituted by one or more radicals selected from the group comprising halogen, alkyl and alkoxy, or in the case where Z is $NR^8$, the radicals $R^7$ and $R^8$ together with the nitrogen atom are also a 5- to 7-membered ring which can contain a further nitrogen or oxygen atom and which can be substituted by one or more substituents selected from the group comprising halogen and alkyl, and $R^x$, $R^6$ and X are as defined in formula I, with compounds of the formula III

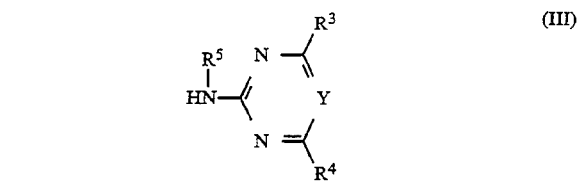

in which $R^3$, $R^4$, $R^5$ and Y are as defined in formula I.

In the abovementioned formulae, alkyl is straight-chain or branched alkyl; this applies analogously to the hydrocarbon moiety in the remaining radicals such as alkoxy, haloalkyl, haloalkoxy, alkylcarbonyl, alkylamino, alkenyl, alkynyl, alkylsulfonyl etc. Halogen is fluorine, chlorine, bromine or iodine, preferably fluorine, chlorine or bromine. Haloalkyl is alkyl which is substituted by one or more halogen atoms. The same applies analogously to haloalkoxy. Unless specifically indicated, a lower alkyl or a radical having 1 to 4 carbon atoms is preferred for the alkyl radicals and the hydrocarbon moiety in the other radicals mentioned.

Particularly interesting processes amongst the processes according to the invention for the preparation of the compounds of the formula I are those in which $R^1X$ is a radical N-$(C_1-C_6)$-alkylsulfonyl-N-$(C_1-C_3)$-alkylamino or $(C_1-C_4)$-alkoxyphenoxy, $R^3$ and $R^4$ independently of one another are $(C_1-C_2)$-alkyl or $(C_1-C_2)$-alkoxy and $R^5$ and $R^6$ are hydrogen or methyl. In this context, $R^1X$ is preferably N-[$(C_1-C_3)$-alkylsulfonyl]-N-[$(C_1-C_2)$-alkyl]-amino, in particular N-(methylsulfonyl)-N-(methyl)-amino, N-(methylsulfonyl)-N-(ethyl)-amino, N-(ethylsulfonyl)-N-(methyl)-amino, N-(ethylsulfonyl)-N-(ethyl)-amino or N-(n-propylsulfonyl)-N-(methyl)-amino or $(C_1-C_3)$-alkoxyphenoxy, in particular 2-methoxyphenoxy, 2-ethoxyphenoxy, 2-n-propoxyphenoxy or 2-isopropoxyphenoxy, $R^3$ and $R^4$ independently of one another are $(C_1-C_2)$-alkyl or $(C_1-C_2)$alkoxy, in particular methyl or methoxy, and $R^5$ and $R^6$ independently of one another are hydrogen or methyl.

Other particularly interesting processes according to the invention are those in which Z is a sulfur atom and $R^7$ is $(C_1-C_4)$-alkyl, in particular methyl or ethyl, phenyl or benzyl, where the aromatic radicals mentioned are unsubstituted or substituted by one or more radicals selected from the group comprising halogen, $(C_1-C_2)$-alkyl and $(C_1-C_2)$-alkoxy, and $R^1$, $R^6$ and X are as defined in formula I Other particularly interesting processes according to the invention are those in which Z is a group of the formula $—NR^8—$, $R^7$ is hydrogen or $(C_1-C_4)$-alkyl, phenyl or benzyl, where the aromatic radicals mentioned are unsubstituted or substituted by one or more radicals selected from the group comprising halogen, $(C_1-C_2)$-alkyl and $(C_1-C_2)$-alkoxy and $R^8$ is hydrogen or $(C_1-C_4)$-alkyl or $R^7$ and $R^8$ together with the nitrogen atom are a 5- to 7-membered ring which can contain a further nitrogen or oxygen atom and which can be substituted by one or more substituents selected from the group comprising halogen and $(C_1-C_4)$-alkyl, for example N-morpholinyl, N-piperidinyl, N-piperazinyl, N-pyrrolidinyl, N-imidazolinyl, N-pyrazolidinyl or N-oxazolinyl, and $R^1$, $R^6$ and X are as defined in formula I.

The yields in the process according to the invention are comparatively high, for example 95% of theory and above, the purities of the sulfonylureas of the formula I formed frequently being above 95% by weight.

The process according to the invention is generally carried out in the presence of an inorganic or organic solvent which is inert under the reaction conditions, or mixtures of two or more suitable solvents. Examples of suitable solvents are aliphatic or, preferably, aromatic, optionally halogenated hydrocarbons, aprotic polar organic solvents such as dialkylalkanoylamides, dialkyl sulfoxides, polyalkylene glycol dialkyl ethers, N-alkylated cyclic amides and nitriles as well as mixtures of the solvents mentioned.

Preferred solvents are, for example, toluene, xylene, chlorobenzene, dimethylformamide, dimethyl sulfoxide, sulfolane, di-, tri- or tetraethylene glycol dialkyl ethers, in particular di-, tri- or tetraethylene glycol dimethyl ether or di-, tri- or tetraethylene glycol diethyl ether, N-methylpyrrolidone, acetonitrile, or else mixtures of two or more of the solvents mentioned.

The process according to the invention can also be carried out in an aqueous, for example purely aqueous, medium.

As a rule, it is advantageous to employ the compound of the formula II in an equimolar amount or in a slight excess relative to the compound of the formula III. Preferred is a molar ratio II:III of 1:1 to 1.2:1, in particular 1:1 to 1.1:1.

The reaction temperatures are preferably 0° C. to 140° C., in particular 20° C. to 132° C.

An advantage of the process according to the invention consists in the fact that the compound of the formula IV $$R^7—Z—H \qquad (IV)$$

in which $R^7$ and Z are as defined above and which is eliminated from the compounds of the formula II, can be recycled quantitatively when carrying out the process according to the invention and reemployed directly in subsequent syntheses to give the compounds of the formula II. If appropriate, the compound of the formula IV can be purified before being recycled, for example simply by distillation.

A further advantage of this process consists in the fact that the use of compounds of the formula V

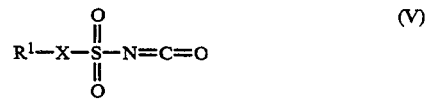

which are employed in conventional processes for the preparation of compounds of the formula I and formed as intermediates under customary reaction temperatures of above 110° C., is avoided. Under these conditions, however, the isocyanates of the formula V can be thermally highly unstable and decompose in some cases, which is then reflected in poor yields (see EP-A-0,131,258, DE-A-2,257,240, G. Lohaus, Chem. Ber. 105, 2791-2799 (1972)).

An additional advantage of the process according to the invention consists in the fact that the solvents can be recycled in virtually quantitative yield since the products of the formula I are obtained from the reaction medium in high purity and yield in the form of sparingly soluble compounds. The solvents can subsequently by purified, for example by distillation, and then recycled to the process.

The starting compounds of the formulae II and III, which are required for the preparation of the compounds of the formula I by the process according to the invention, can be prepared by processes some of which are known from the literature.

For example, the heterocycles of the formula III are either commercially available or can be prepared with ease by suitable laboratory methods; see, for example, U.S. Pat. No. 4,310,470; EP-A-0,027,200; U.S. Pat. No. 4,299,960; M. J. Langemann, C. K. Banks, *J. Am. Chem. Soc.* 73, 3011 (1951).

The compounds of the formula II are novel and can be obtained analogously to customary methods (see, for example, Tietze and Eicher in "Reaktionen und Synthesen" [Reactions and Syntheses], p. 92, Thieme Verlag, Stuttgart 1981, or Houben-Weyl, Vol. IX, p. 636) by reacting the corresponding sulfonamides VI with the corresponding acid chlorides VII,

which, in turn, are accessible by standard laboratory methods (see, for example, for compounds of the formula VI, Houben-Weyl, Ergänzungsband [Supplement] E11, p. 1015 et seq.; for compounds of the formula VII see, for example, W. A. Thaler, *J. Chem. Soc. Chem. Communications* 1968, 527).

The smooth course of the process according to the invention and the high yield must be regarded as surprising since the starting material of the formula II contains several activated, electrophilic and nucleophilic centers. In particular, all of the electrophilic centers can react, in principle, with the nucleophilic substances of the formula III and thus give a large number of by-products due to fragmentation reactions; cf. Beyer, Lehrbuch der Organischen Chemie [Textbook of Organic Chemistry], 19th Edition, p. 128, Hirzel Verlag Stuttgart, according to which sulfonyl groups and phenoxy groups are very good leaving groups.

Accordingly, the process according to the invention represents a novel, simple, highly selective process for the synthesis of the compounds of the formula I in virtually quantitative yields and can also be reproduced on a larger industrial scale. The process can be carried out continuously or batchwise.

EXAMPLES

Preparation methods for 1-[(N-methylsulfonyl-N-methyl-amino)-sulfonyl]-3-(4,6-dimethoxy-2-pyrimidyl)-urea 1) From S-benzyl N-(N'-methyl-N'-methylsulfonyl-amino-sulfonyl)-thiocarbamate 33.9 g of S-benzyl N-(N'-methyl-N'-methylsulfonyl-amino-sulfonyl)-thiocarbamate (formula II, $R^1$ is $CH_3$, X is $SO_2NCH_3$, $R^6$ is H, Z is S, $R^7$ is benzyl) are stirred together with 15.5 g of 2-amino-4,6-dimethoxypyrimidine for 2.5 hours at 70° C. in 60 ml of toluene. After cooling to 5° C., the precipitate is filtered off, washed with 60 ml of toluene and dried. This gives 36.7 g of the desired product of the formula (I) in the form of a white powder of melting point 175°–177° C. The purity is 97.1% by weight according to HPLC analysis, which corresponds to a yield of 96.6% of theory.

2) From S-methyl N-(N'-methyl-N'-methylsulfonyl-aminosulfonyl)-thiocarbamate 26.3 g of S-methyl N-(N'-methyl-N'-methylsulfonyl-amino-sulfonyl)-thiocarbamate (formula II, $R^1$ is $CH_3$, X is $SO_2NCH_3$, $R^6$ is H, Z is S, $R^7$ is methyl) together with 15.5 g of 2-amino-4,6-dimethoxypyrimidine are stirred for 2 hours at 75° C. in 100 ml of chlorobenzene. The mixture is allowed to stand overnight at room temperature, and the resulting precipitate is filtered off and washed with 30 ml of chlorobenzene. This gives 37.2 g of the desired product of the formula (I) with an HPLC purity of 94.6% by weight, which corresponds to a yield of 95.4% of theory. The melting point of the product is 172°–174° C.

3) From N-(N'-methyl-N'-methylsulfonyl-aminosulfonyl)-urea 23.2 g of N-(N'-methyl-N'-methylsulfonyl-aminosulfonyl)-urea (formula II, $R^1$ is $CH_3$, X is $SO_2NCH_3$, $R^6$ is H, Z is $NR^8$, $R^8$ is H, $R^7$ is H) together with 15.5 g of 2-amino-4,6-dimethoxypyrimidine in 150 ml of chlorobenzene are stirred for 2 hours at 35° C. while blowing in catalytic amounts of ammonia. The precipitated product is subsequently filtered off with suction, washed with 50 ml of chlorobenzene and dried. 36.4 g of the desired product of the formula (I) with an HPLC purity of 96.4% by weight are obtained, which corresponds to a yield of 95.1% of theory. The melting point of the product is 173°–175° C.

4) From N-[(N'-methyl-N'-methylsulfonyl-aminosulfonyl)-aminocarbonyl]-morpholine 26.3 g of N-[(N'-methyl-N'-methylsulfonyl-aminosulfonyl)aminocarbonyl]-morpholine (formula II, $R^1$ is $CH_3$, X is $SO_2NCH_3$, $R^6$ is H, Z is $NR^8$, $NR^8R^7$ is N-morpholinyl) are stirred together with 15.5 g of 2-amino-4,6-dimethoxypyrimidine for 6 hours at 75° C. in 100 ml of toluene. After cooling to 5° C., the precipitate is filtered off, washed with 20 ml of toluene and dried. This gives 35.9 g of the desired product of the formula (I) with an HPLC purity of 97.6% by weight, which corresponds to a yield of 95.0% of theory. The melting point of the product is 174°–175° C.

We claim:

1. A process for the preparation of a compound of the formula (I) or a salt thereof

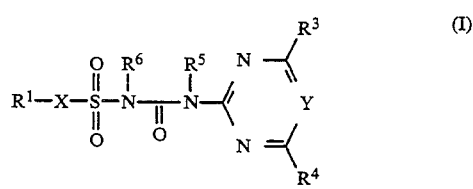

in which

X is oxygen, $-ONR^2-$ or $-SO_2-NR^2-$,

Y is nitrogen or CH, $R^1$ is $(C_1-C_6)$-alkyl, $(C_2-C_6)$-alkenyl or $(C_2-C_6)$-alkynyl, where each of the 3 radicals is unsubstituted or mono- or polysubstituted by radicals selected from the group consisting of halogen, $(C_1-C_4)$-alkoxy and $(C_1-C_4)$alkoxycarbonyl, or, in the case where X is oxygen, also phenyl which is unsubstituted or substituted by one or more radicals selected from the group consisting of halogen, nitro, $(C_1-C_4)$-alkyl, $(C_1-C_4)$-haloalkyl, $(C_1-C_4)$-alkoxy, $(C_1-C_4)$ haloalkoxy or $(C_1-C_4)$-alkoxycarbonyl, $R^2$ is hydrogen, $(C_1-C_6)$-alkyl, $(C_2-C_6)$-alkenyl, $(C_2-C_6)$-alkynyl or $(C_3-C_6)$-cycloalkyl, $R^3$ and $R^4$ independently of one another are hydrogen, $(C_1-C_4)$-alkyl or $(C_1-C_4)$-alkoxy, where each of the two last-mentioned radicals is unsubstituted or mono- or polysubstituted by radicals selected from the group consisting of halogen, alkoxy and alkylthio, or are halogen, $(C_1-C_4)$-alkylthio, $(C_1-C_4)$-alkylamino or di-amino and $R^5$ and $R^6$ independently of one another are hydrogen or $(C_1-C_4)$-alkyl, which comprises reacting a compound of the formula II

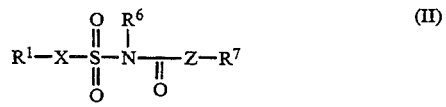

in which

Z is a sulfur atom or a group of the formula $-NR^8-$ and $R^7$ and $R^8$ independently of one another are hydrogen, $(C_1-C_6)$alkyl, phenyl or benzyl, the abovementioned aromatic radicals being unsubstituted or substituted by one or more radicals selected from the group consisting of halogen, alkyl and alkoxy, or in the case where Z is $NR^8$, the radicals $R^7$ and $R^8$ together with the nitrogen atom are also a 5- to 7-membered ring which can be substituted by one or more substituents selected from the group consisting of halogen, and alkyl, and $R^1$, $R^6$ and X are as defined in formula I, with a compound of the formula III

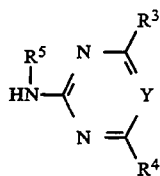
(III)

in which $R^3$, $R^4$, $R^5$ and Y are as defined in formula I, wherein the reaction is carried out in the presence of an inert organic solvent at a temperature in the range of 0°–140° C.

2. The process as claimed in claim 1, wherein the temperatures are in the range from 20° C. to 132° C.

3. The process as claimed in claim 1, wherein the molar ratio II:III is in the range of from 1:1 to 1.2:1.

4. The process as claimed in claim 1, wherein $R^1X$ is N-($C_1$–$C_6$)-alkylsulfonyl-N-($C_1$–$C_3$)-alkyl-amino or ($C_1$–$C_4$)-alkoxyphenoxy, $R^3$ and $R^4$ independently of one another are ($C_1$–$C_2$)-alkyl or ($C_1$–$C_2$)-alkoxy and $R^5$ and $R^6$ are hydrogen or methyl.

5. The process as clawed in claim 1, wherein $R^1X$ is N-[($C_1$–$C_3$)-alkylsulfonyl]-N-[($C_1$–$C_2$)-alkyl]N-amino or ($C_1$–$C_3$)-alkoxyphenoxy and $R^3$ and $R^4$ independently of one another are ($C_1$–$C_2$)-alkyl or ($C_1$–$C_2$)-alkoxy and $R^5$ and $R^6$ are hydrogen or methyl.

6. The process as claimed in claim 1, wherein, in formula II,
Z is a sulfur atom and $R^7$ is ($C_1$–$C_4$)-alkyl, phenyl or benzyl, where the aromatic radicals mentioned are unsubstituted or substituted by one or more radicals selected from the group consisting of halogen, ($C_1$–$C_2$)-alkyl and ($C_1$–$C_2$)-alkoxy, and $R^1$, $R^6$ and X are as defined in formula I.

7. The process as claimed in claim 1, wherein, in formula II,
Z is a group of the formula —$NR^8$—, $R^7$ is hydrogen or ($C_1$–$C_4$)-alkyl, phenyl or benzyl, where the aromatic radicals mentioned are unsubstituted or substituted by one or more radicals selected from the group consisting of halogen, ($C_1$–$C_2$)-alkyl and ($C_1$–$C_2$)-alkoxy and $R^8$ is hydrogen or ($C_1$–$C_4$)-alkyl, or
$R^7$ and $R^8$ together with the nitrogen atom are a 5- to 7-membered ring which can contain a further nitrogen or oxygen atom and can be substituted by one or more substituents selected from the group consisting of halogen, and ($C_1$–$C_4$)-alkyl,
and $R^1$, $R^6$ and X are as defined in formula I.

8. The process as clawed in claim 1, wherein the compound of the formula II is employed in an equimolar amount or in a slight excess relative to the compound of the formula III.

9. The process as claimed in claim 8, wherein the molar ratio II:III is in the range of from 1:1 to 1.2:1.

* * * * *